United States Patent [19]
Hurley et al.

[11] Patent Number: 5,969,271
[45] Date of Patent: Oct. 19, 1999

[54] AMBIENT SAMPLER WITH RAIN PROTECTION

[75] Inventors: John F. Hurley, Easton; John N. Dale, Stratford; Bruce E. Hartel, Shelton, all of Conn.

[73] Assignee: Combustion Components Associates, Inc., Monroe, Conn.

[21] Appl. No.: 08/933,053

[22] Filed: Sep. 18, 1997

[51] Int. Cl.⁶ .............................. G01N 1/00; G01W 1/00
[52] U.S. Cl. ..................... 73/863.01; 73/863.23; 73/170.17
[58] Field of Search .................. 73/863.01, 863.23, 73/863.42, 170.17; 346/33 R, 60; 454/342; 52/1, 66

[56] References Cited

U.S. PATENT DOCUMENTS

| | | |
|---|---|---|
| 4,245,499 | 1/1981 | Nguyen et al. . |
| 5,035,091 | 7/1991 | Ebato . |
| 5,123,875 | 6/1992 | Eubank et al. . |
| 5,533,391 | 7/1996 | Brade et al. . |

*Primary Examiner*—Benjamin R. Fuller
*Assistant Examiner*—Abdullahi Aw-Musse
*Attorney, Agent, or Firm*—Barry R. Lipsitz

[57] ABSTRACT

Apparatus is provided for collecting samples of fallout, such as power plant stack emissions, from the environment. A collector substrate is adapted to progressively present a fresh collection surface for the collection of fallout from the environment over time. An opening is disposed between the substrate and the environment to allow the fallout to reach the substrate. A cover is provided for the opening. The cover is automatically closed in the presence of rain to protect the substrate from rainwater, and automatically opened after rain terminates to allow the substrate to collect fallout. Mechanical and electrical embodiments are disclosed for the automatic cover.

20 Claims, 5 Drawing Sheets

AMBIENT SAMPLER WITH RAIN PROTECTION

BACKGROUND OF THE INVENTION

The present invention relates to ambient samplers for monitoring power plant stack emissions, ambient emissions and other environmental fallout. More particularly, the invention concerns apparatus for protecting the collection surface of such devices from rain.

Apparatus for monitoring environmental fallout generally comprises a collection surface for the collection of fallout from the environment over time. The surface can comprise any suitable material, such as a paper substrate that can then be removed from the collection device and analyzed. One type of ambient sampler has a collection disk that rotates over time. For example, the disk may rotate one revolution each twenty-four hours. A collection opening allows fallout to enter the apparatus and to settle on the collection disk. Such apparatus allows a time resolvable record to be established of "fallout emissions" from industrial processes such as power plant stacks.

While such apparatus functions suitably under dry conditions, the entry of rain water into the collection opening can wash away the collected samples and interfere with accurate analysis of fallout emissions. This is a particular problem in wet climates, such as on the island of Hawaii where it rains frequently and heavily each day.

It would be advantageous to provide automatic and self-restoring protection from rain in an ambient sampler. It would be further advantageous if apparatus could be provided to afford rain protection without the need for any external power source. The present invention provides apparatus for protecting an ambient sampler from rain, having the aforementioned and other advantages.

SUMMARY OF THE INVENTION

In accordance with a first embodiment of the invention, rain protection is provided for an ambient sampler without the need for any motive power other than rain and gravity. In particular, apparatus in accordance with such an embodiment is provided for collecting samples of fallout from an environment. The apparatus comprises a collector substrate adapted to progressively present a fresh collection surface for the collection of fallout from the environment over time. An opening is disposed between the substrate and the environment to allow the fallout to reach the substrate. A cover is provided for the opening. Actuation means are provided to automatically close the cover in the presence of rain to protect the substrate from rain and automatically open the cover after the rain terminates to allow the substrate to collect fallout.

In the first embodiment, at least one receptacle is provided for collecting rainfall. The receptacle is supported from a pivotally mounted shaft so that the shaft rotates in a first direction when the receptacle fills with rain water and in an opposite direction when the receptacle empties. The cover is actuated to cover the opening when the shaft rotates in the first direction and to uncover the opening when the shaft rotates in the opposite direction.

The receptacle can include an opening for draining collected rainwater therefrom upon cessation of rainfall. In an illustrated embodiment, the receptacle is a trough with a weep hole in a bottom portion thereof.

The cover can be supported from the shaft. More specifically, an arm can extend from the shaft, the arm having a first end for supporting the cover. A counterweight adjacent to a second end of the arm counterbalances the cover. The counterweight can be adjustable.

The shaft can support a first receptacle at a first end thereof and a second receptacle at a second end thereof. In such an embodiment, the arm which supports the cover may extend from a central portion of the shaft.

The collector substrate can comprise a substantially horizontal disk mounted on a rotatable spindle. The disk provides a fresh collection surface as it rotates.

In the first embodiment, the actuation means are responsive to the weight of rainwater for closing the cover. Similarly, the actuation means are responsive to the draining of the rainwater for opening the cover. More generally, the actuation means rely on gravity to close and open the cover.

In another embodiment, the actuation means comprise a sensor for detecting rainfall. An electric actuator is provided, which is responsive to the sensor, for closing and opening the cover. For example, the sensor can comprise an electric sensor.

The apparatus can further comprise a housing for the collector substrate, wherein the cover and actuation means comprise an assembly mounted to the housing. In an illustrated embodiment, the assembly includes a track for guiding the cover over the opening. The electric actuator slides the cover in the track to cover and uncover the opening. The electric actuator can comprise, for example, a motor or solenoid.

The cover can include a weep hole for allowing rainwater to dribble therethrough. In such an embodiment, the collector substrate is provided with a water soluble agent responsive to the dribbling rainwater, in order to record the occurrence of rain on the collector substrate. Where the collector substrate is a disk, the water soluble agent may be water soluble ink provided around the periphery of the disk.

DETAILED DESCRIPTION OF THE INVENTION

Figure 1:
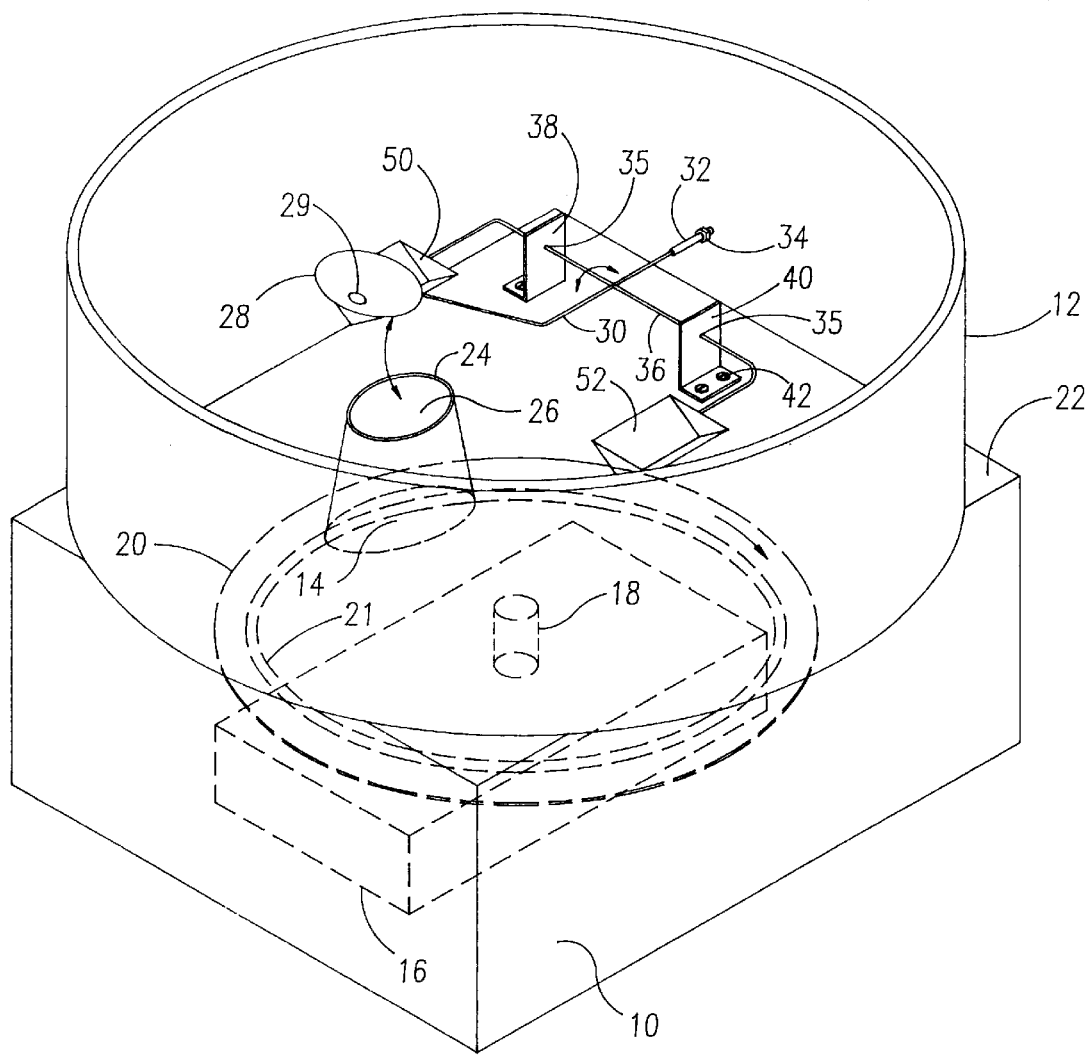
FIG. 1 is a perspective schematic view of a first embodiment of apparatus in accordance with the present invention.

FIG. 1 illustrates an ambient sampler comprising a housing 10 which contains a collector substrate 20 in the form of a disk which is rotated via shaft 18 driven by a drive 16. Drive 16 can comprise, for example, an electric motor which drives shaft 18 via a suitable gearing or belt and pulley means as well known in the art. The speed of rotation is set in order to provide a time resolvable record of fallout emissions impinging on collector substrate 20 via a collection opening 26 in conduit "sampler inlet tube" 24. For example, drive 16 can be arranged to rotate disk 20 one revolution per 24 hours. Such a rotation speed, coupled with an opening 26 on the order of two inches in diameter and a collector substrate 20 on the order of twelve inches in diameter, will provide a time resolvable record of fallout emissions.

Housing 10 includes a top surface 22 which has an opening 14 corresponding to the opening 26 in conduit 24. Top surface 22 also supports a cover actuation assembly via support brackets 38, 40 which are mounted to the top surface 22 via fasteners (e.g., nuts and bolts) 42. The support brackets shown are for purposes of illustration only, and it will be appreciated that many other types of support elements may be used, which may be more sophisticated than the simple brackets 38, 40 and include, for example, bearing means and the like for supporting a shaft 36.

Shaft 36 together with an arm 30 and troughs 50, 52 provide an actuation device for automatically closing opening 24 with a cover 28 in the presence of rain. In this manner, the collector substrate 20 is protected from rainwater. Cover 28 has a small hole 29 which allows a small amount of rainwater to contact the collector substrate 20. The substrate 20 has a ring of water soluble ink 21 on its outer periphery which will "blur" when contacted by water dribbling through hole 29. When the collector substrate is later retrieved for analysis, the blur will indicate that the cover was closed and it was raining at the points in time corresponding to the blur.

Cover 28 is supported by arm 30. The cover can be mounted to the arm by any suitable means, such as by spot welding, fastener hardware, an adhesive, or the like. Similarly, arm 30 can be mounted to shaft 36 via any suitable means such as spot welding, adhesive, or fastener hardware. An adjustable counterweight is provided at the end of arm 30 opposite from cover 28 via a threaded weight 32 and nut 34. Nut 34 is screwed on to a corresponding threaded portion of weight 32, and can be rotated clockwise or counterclockwise on weight 32 in order to adjust the effective counterbalancing force. Shaft 36 is adapted to rotate within brackets 38, 40 to provide a pivoting arrangement allowing cover 28 to close and open opening 26. In the simplest embodiment, brackets 38, 40 comprise holes 35 through which shaft 36 passes, the diameter of holes 35 being slightly larger than the outside diameter of shaft 36. As noted above, the pivoting action can be improved by providing bearings, such as sleeve bearings well known in the art, between shaft 36 and holes 35.

Figure 2:
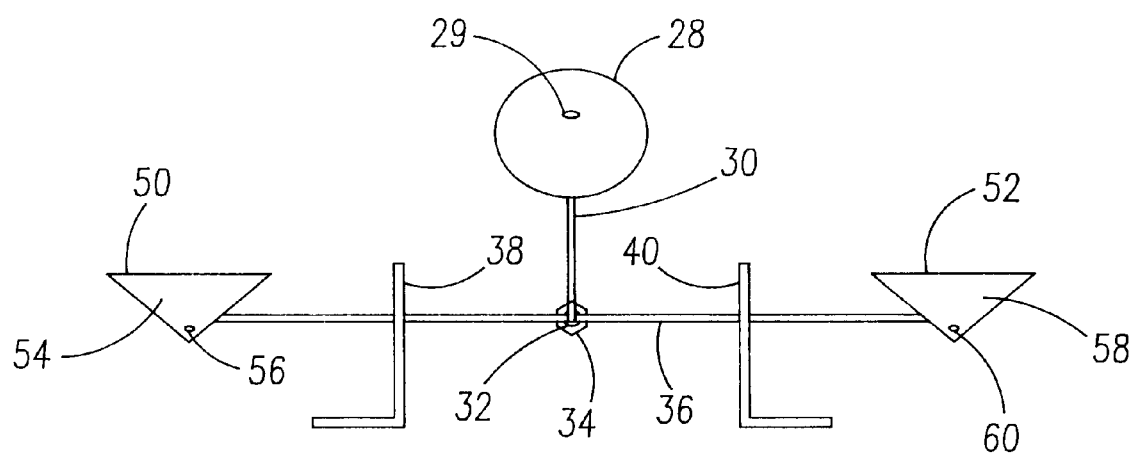
FIG. 2 is a front view of the cover actuation mechanism used in the embodiment of FIG. 1.
Figure 3:
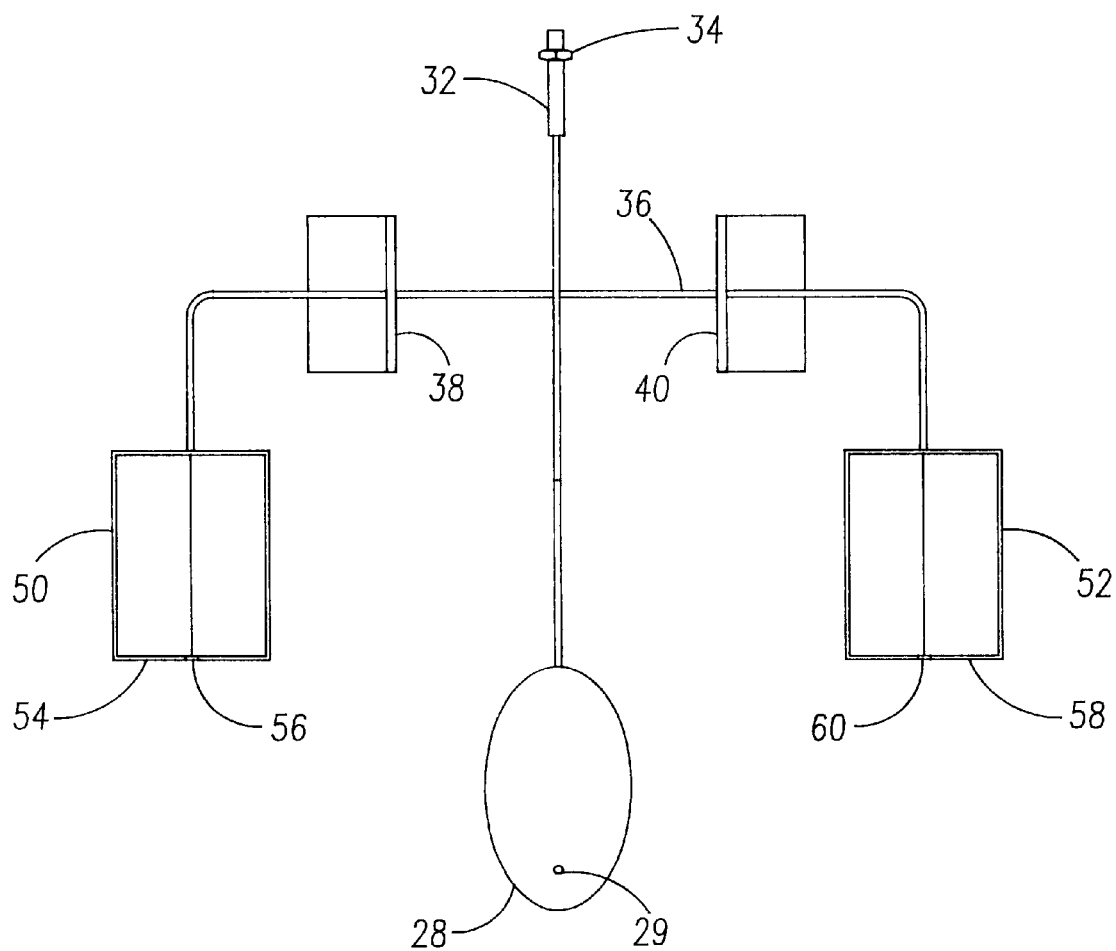
FIG. 3 is a top view of the cover actuation mechanism of FIG. 2.
Figure 4:
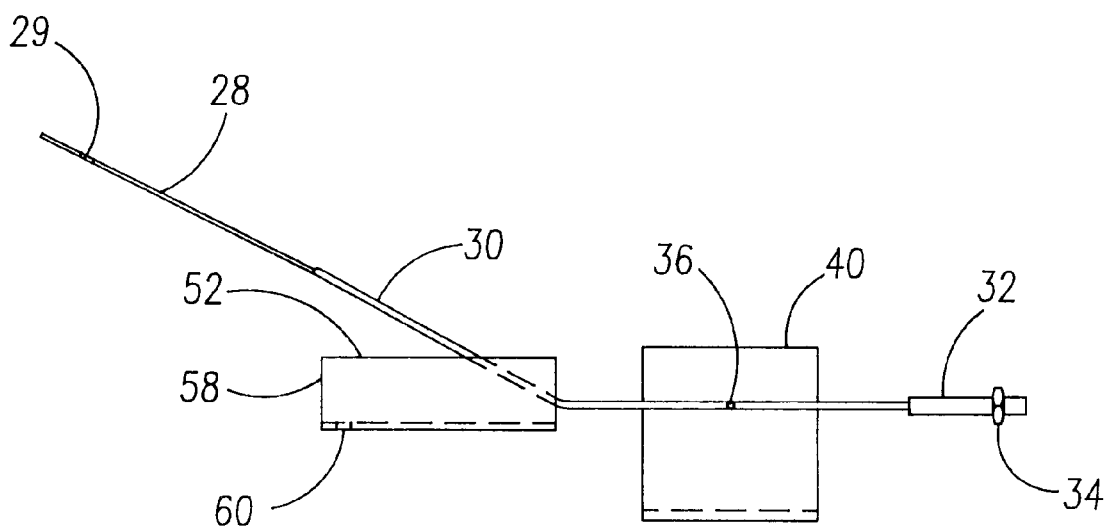
FIG. 4 is a side view of the cover actuation mechanism of FIG. 2.

In operation, arm 30 and cover 28 are rotatable due to the pivoting action provided by shaft 36 in brackets 38, 40. The troughs 50, 52 are provided to collect rainwater. As best shown in FIG. 2, trough 50 includes an end wall 54 having a weep hole 56. Similarly, trough 52 includes an end wall 58 having an weep hole 60. When it is not raining, the cover 28 is held off of the sampler inlet conduit 24 by the counterbalance 32. When rain starts, the troughs 50, 52 collect rainwater. The slight weight of the rainwater overcomes the sensitive counterbalance and the cover 28 rotates to a closed position, covering opening 26 in conduit 24. Weep holes 56, 60 in the troughs allow a slight water leakage. During rain, the leakage is small enough that the cover 28 will not open. When the rain stops, the rainwater in troughs 50 and 52 drain out from the troughs due to the leakage via weep holes 56, 60, until the weight is reduced enough to allow the cover 28 to open. The apparatus is self-maintaining in this respect, and no motive power other than the rain and gravity is required.

An optional wind and dust baffle 12 can be provided on housing 10. Baffle 12 can be in the shape of a simple cylinder as shown, or can comprise an extension of the sidewalls from the housing. Other arrangements will be apparent to those skilled in the art.

Figure 5:
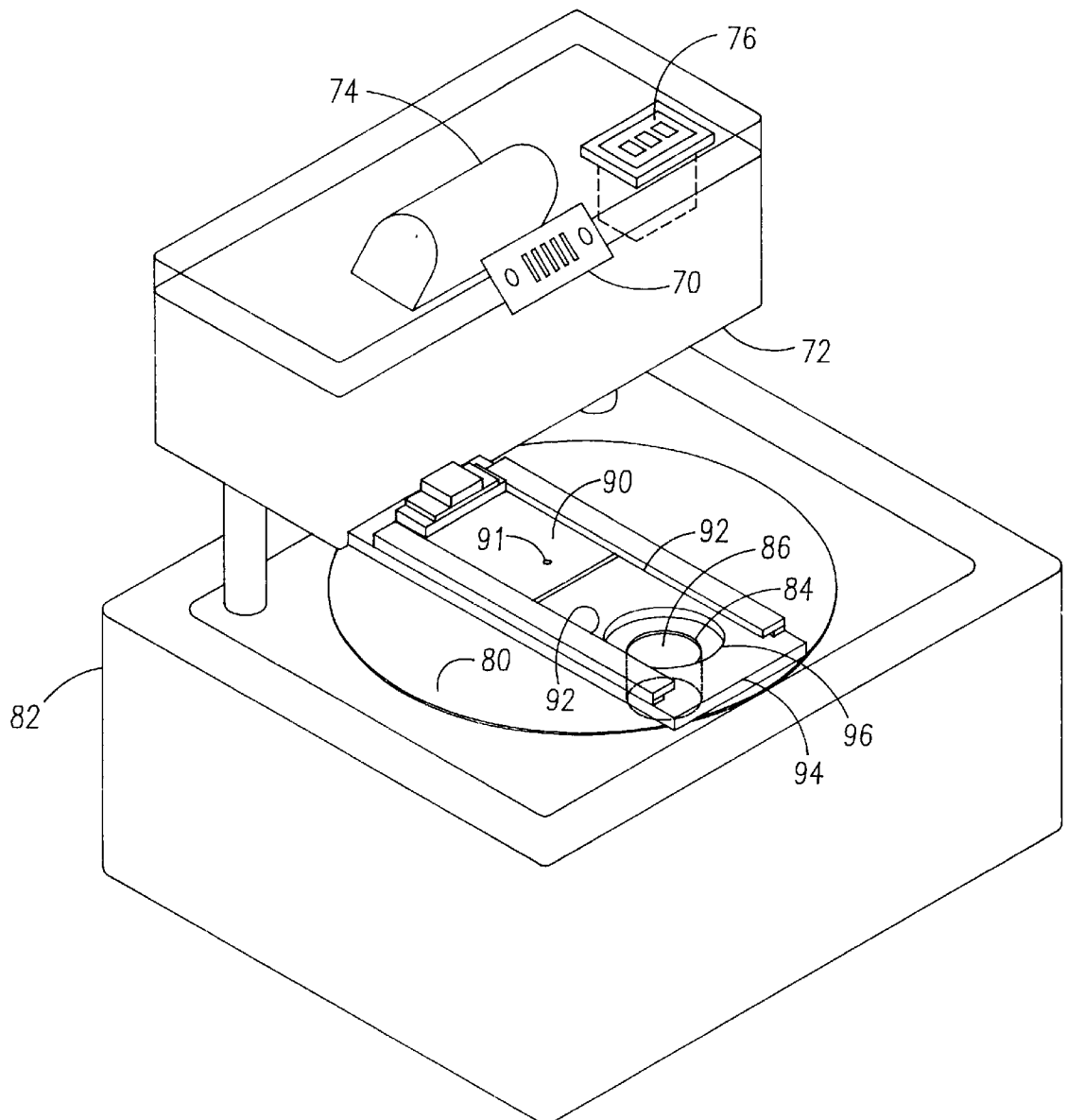
FIG. 5 is a schematic perspective view of an electrically actuated embodiment of the present invention.

FIG. 5 illustrates an alternate embodiment in which a rain sensor 70 is used to actuate an electric motor 74 to close and/or open a cover 90 for the sampler inlet tube 84. Rain sensor 70 can comprise, for example, a substrate having a plurality of spaced conductors that when dampened, will close a switch by the conduction of electric current through the moisture. Such sensors are well known in the art as indicated, for example, in U.S. Pat. No. 4,245,499 to Nguyen, et al. Any other type moisture detector known in the art can also be used.

Upon detection of rain, sensor 70 will actuate motor 74 via controls 76 to slide cover 90 within tracks 92 to cover opening 96 in plate 94. The opening 96 is disposed over the ambient sampler inlet tube 84 which has a corresponding opening 86. When the cover 90 is retracted such that openings 96 and 86 are not closed, tube 84 will allow fallout from the environment to collect on the surface of collection disk 80. When rain is detected, the closing of cover 90 over openings 96 and 86 will prevent rainwater from impinging on collection disk 80. Thus, samples collected prior to and after the occurrence of rain will not be ruined by the rainwater. As in the previous embodiment, the cover 90 can be provided with a small hole 91 which allows rainwater to dribble therethrough. Upon contacting the collection disk 80, which may be provided with a ring of water soluble ink on its periphery, the water will blur the ink to indicate that it had rained and the cover was closed.

Sensor 70 can be mounted on a housing 72 that encloses motor 74 and controls 76. Motor 74 is adapted to actuate sliding cover 90 via a conventional gearing arrangement or the like. In an alternate embodiment, motor 74 can be replaced by a solenoid or other electrically actuable device. The collection disk 80 is mounted within a housing 82 to which the housing 72 is mounted. A lid on housing 82 is openable to enable the removal of collection disk 80 and the analysis of deposits collected thereon. It should be understood that while the cover of housing 82 is shown broken away in FIG. 5, the actual cover is continuous except for an opening that accommodates inlet tube 84. In this manner, collection disk 80 is protected from the elements except in the limited area defined by opening 86 of inlet tube 84.

It should now be appreciated that the present invention provides an automatic rain protection device for an ambient sampler. Upon the occurrence of rain, a cover is automatically caused to close the sampler opening to protect the collection substrate from the adverse effects of rainwater. When the rain ceases, the cover automatically opens to reexpose the collection surface to the environment for the collection of fallout.

Although the invention has been described in connection with various specific embodiments, it should be appreciated that numerous modifications and adaptations may be made thereto without departing from the scope of the inventions as set forth in the claims.

We claim:

1. Apparatus for collecting samples of fallout from an environment, said apparatus comprising:
    a collector substrate adapted to progressively present a fresh collection surface for the collection of fallout from said environment over time;
    an opening disposed between said substrate and said environment to allow said fallout to reach said substrate;
    a cover for said opening; and
    actuation means comprising at least one member responsive to rainwater for automatically closing said cover in the presence of rain to protect said substrate from rainwater and automatically opening said cover after said rain terminates to allow said substrate to collect said fallout.

2. Apparatus in accordance with claim 1 wherein said member comprises:

at least one receptacle for collecting rainfall, said receptacle being supported from a pivotally mounted shaft so that said shaft rotates in a first direction when said receptacle fills with rainwater and in an opposite direction when said receptacle empties;

said cover being actuated to cover said opening when said shaft rotates in said first direction and to uncover said opening when said shaft rotates in said opposite direction.

3. Apparatus in accordance with claim 2 wherein said receptacle has an opening for draining collected rainwater therefrom upon cessation of rainfall.

4. Apparatus in accordance with claim 3 wherein said receptacle is a trough with a weep hole in a bottom portion thereof.

5. Apparatus in accordance with claim 2 wherein said cover is supported from said shaft.

6. Apparatus in accordance with claim 2 further comprising:

an arm extending from said shaft and having a first end for supporting said cover; and a counterweight adjacent to a second end of said arm for counterbalancing said cover.

7. Apparatus in accordance with claim 6 wherein said shaft supports a first receptacle at a first end thereof and a second receptacle at a second end thereof.

8. Apparatus in accordance with claim 7 wherein said arm extends from a central portion of said shaft.

9. Apparatus in accordance with claim 6 wherein said counterweight is adjustable to adjust the sensitivity of said actuation means.

10. Apparatus in accordance with claim 1 wherein said collector substrate comprises a substantially horizontal disc mounted on a rotatable spindle, said disc providing said fresh collection surface as it rotates.

11. Apparatus in accordance with claim 1 wherein said actuation means are responsive to the weight of rainwater for closing said cover.

12. Apparatus in accordance with claim 11 wherein said actuation means are responsive to the draining of said rainwater for opening said cover.

13. Apparatus in accordance with claim 1 wherein said actuation means rely on gravity to close and open said cover.

14. Apparatus in accordance with claim 1 wherein said member comprises:

a sensor for detecting rainfall; and an electric actuator responsive to said sensor for closing and opening said cover.

15. Apparatus in accordance with claim 14 wherein said sensor is an electric sensor.

16. Apparatus in accordance with claim 14 further comprising a housing for said collector substrate, wherein said cover and actuation means comprise an assembly mounted to said housing.

17. Apparatus in accordance with claim 16 wherein said assembly includes a track for guiding said cover over said opening, and said electric actuator slides said cover in said track to cover and uncover said opening.

18. Apparatus in accordance with claim 1 wherein:

said cover includes a weep hole for allowing rainwater to dribble therethrough; and said collector substrate includes a water soluble agent responsive to rainwater dribbling through said weep hole to record the occurrence of rain.

19. Apparatus in accordance with claim 18 wherein:

said collector substrate comprises a substantially horizontal disk mounted on a rotatable spindle, said disk providing said fresh collection substrate as it rotates; and said water soluble agent is provided around the periphery of said disk.

20. Apparatus in accordance with claim 19 wherein said water soluble agent comprises water soluble ink.

* * * * *